United States Patent [19]

Melgui et al.

[11] Patent Number: 4,641,093
[45] Date of Patent: Feb. 3, 1987

[54] METHOD AND DEVICE FOR MAGNETIC TESTING OF MOVING ELONGATED FERROMAGNETIC TEST PIECE FOR MECHANICAL PROPERTIES BY UTILIZING THE MAGNITUDE OF REMANENT MAGNETIC FLUX AND A PULSED MAGNETIC FIELD

[75] Inventors: Mikhail A. Melgui; Sergei G. Sandomirsky, both of Minsk, U.S.S.R.

[73] Assignee: Institut Prikladnoi Fiziki Akademii Nauk Belorusskoi SSR, Minsk, U.S.S.R.

[21] Appl. No.: 476,879

[22] PCT Filed: Jul. 28, 1981

[86] PCT No.: PCT/SU81/00062
§ 371 Date: Mar. 22, 1983
§ 102(e) Date: Mar. 22, 1983

[87] PCT Pub. No.: WO83/00559
PCT Pub. Date: Feb. 17, 1983

[51] Int. Cl.[4] .................. G01N 27/72; G01R 33/12
[52] U.S. Cl. .................................. 324/239; 324/262
[58] Field of Search ............... 324/211, 212, 222, 223, 324/239–243, 262

[56] References Cited

U.S. PATENT DOCUMENTS 3,586,963  4/1969  Arrott et al. .................. 324/243
3,940,690  4/1976  Suhr et al. .................... 324/242
4,044,302  8/1977  Mayberry ...................... 324/223

FOREIGN PATENT DOCUMENTS 1473516   5/1976   Fed. Rep. of Germany .
2274917   6/1975   France .
  29109   8/1978   Japan .
1498218   1/1978   United Kingdom .
 696369  11/1979   U.S.S.R. .
1096564   6/1984   U.S.S.R. .
1108353   8/1984   U.S.S.R. .

Primary Examiner—Ernest F. Karlsen
Assistant Examiner—Walter E. Snow
Attorney, Agent, or Firm—Fleit, Jacobson, Cohn & Price

[57] ABSTRACT

A method comprises magnetizing a portion of the test piece by a pulsed magnetic field and forming as a result of said magnetizing two regions of remanent magnetization, which are magnetized to saturation in opposite directions, determining the magnitude of the remanent induction, which magnitude is used to judge the mechanical properties of the test piece. The magnitude of the remanent induction is determined by converting its gradient along the magnetized portion to an electrical signal, selecting from said signal a one-polarity pulse indicative of the change in the remanent induction between said regions, and integrating said selected pulse. A device comprises a pulse generator 1, magnetizing coils 2 connected to said generator in antiparallel relationship and arranged along the test piece, a transducer 4 for converting a gradient to an electrical signal, a measuring circuit including a key 5 and an integrator 6. There is also provided a comparison circuit 7 adapted to select an instant of time at which the signal at the output of the transducer 4 assumes a zero value.

3 Claims, 6 Drawing Figures

METHOD AND DEVICE FOR MAGNETIC TESTING OF MOVING ELONGATED FERROMAGNETIC TEST PIECE FOR MECHANICAL PROPERTIES BY UTILIZING THE MAGNITUDE OF REMANENT MAGNETIC FLUX AND A PULSED MAGNETIC FIELD

TECHNICAL FIELD

The invention relates to methods of nondestructive testing of materials and articles, and more specifically is concerned with a magnetic inspection of a moving elongated ferromagnetic test piece for determining mechanical properties thereof and a device for carrying out the same.

BACKGROUND ART

It is a common knowledge that magnetic and mechanical properties of ferromagnetic materials, for instance steel, depend on their chemical composition and structure obtained during their manufacture. Therefore, manufacturing a steel possessing desirable melchanical properties, such as hardness, ultimate strength, yield strength, and elongation, may be ensured by maintaining the chemical composition constant and the manufacturing process stable. Since one and the same departure (within tolerance limits) from a chemical composition and the manufacturing process employed cause changes both in mechanical and magnetic properties, there exists a correlation dependence between these properties, which allow determining mechanical properties by measuring magnetic properties. The best magnetic properties for the above purpose are a coercive force and a remanent induction (or magnetization).

In a known in the art method entitled as "Method for measuring remanent magnetization" (cf. Japan accepted patent specification No. 53-29109, Int. Cl. G 01n 27/68) the test piece (plate) is passed between two electromagnets disposed in opposing relationship at the both sides of said plate, one at the top side and the other one at the underside. The electromagnets provides formation of a magnetic track in the test material, which magnetic track extends in the direction of movement of said test material. Located some distance from said electromagnets are transducers mounted for movement along a path crossing said magnetic track. The signal from the transducer is used to determine the quantity of remanent magnetization in the test plate. The inspection results in this method are influenced by displacement of the test material due to vibration, which affects the accuracy of measurement.

Furthermore, the presence of moving parts makes carrying out this method more difficult and impairs the reliability thereof.

In another known in the art method entitled as "Method and apparatus for detecting the presence of magnetic anomalies in ferromagnetic and non-ferromagnetic materials" (cf. U.K. Pat. No. 1,498,218, Int. Cl. G 01n 27/86) the test material is passed through a ring magnet so that said test material is magnetized by the magnet field. The parameters of the test material are determined by the magnitude of signals formed in the sensing coils under the action of the magnetic dipoles set up in the test material. The amplitudes of the thus produced signals representative of the properties of the test material are proportional to the magnitude of the magnetic dipoles and velocity of the test material.

The above-mentioned dependence of the output signal on the velocity of the test material affect the accuracy of the method.

There is also known a method for magnetic inspection of moving ferromagnetic articles of round section (cf. USSR Author's Certificate No. 696,369, 5.11.79) which comprises a pulse generator adapted to generate magnetizing pulses with a variable frequency of pulse repetition. The magnetizing means are made in the form of solenoids placed in antiparallel relationship in the circuit of the pulse generator. Inside one of the solenoids are mounted reading devices symmetric about the axis of said solenoid. As reading devices use is made of a convential ferroprobe-gradiometers which are placed in a circuit so that their output signals are summed. Field coils of the ferroprobes are connected through power amplifiers to an exciting circuit, and measuring coils are connected to the input of a selective amplifier tuned to the second harmonic.

Magnetic testing of the material for mechanical properties with the use of the above method is carried out as follows.

The test piece is passed inside the magnetizing solenoids and between the ferroprobe-gradiometers. A pulsed current is passed through the coils of the magnetizing solenoids to form magnetic marks. The parameters of said pulses are selected so as to form a maximum gradient of the remanent field. The frequency of repetition of the magnetizing pulses is selected depending on the velocity of the moving test piece so that while passing by the magnetic marks there is no remanent magnetic field inside the second solenoid. The ferroprobe-gradiometers are responsive to a gradient which is normal to the direction in which the remanent magnetic field component is moving, said gradient being representative of the mechanical properties of the test body. When the test piece in its motion between the ferroprobes is maintained evenly spaced therefrom their signals are equal, and the combined signal is equal to the sum of all the signals. In case the test piece is caused to displace from the center line of its movement path the strength of signals from the ferroprobes located at one side increases, while the strength of signals from the ferroprobes located at the other side decrease, but the sum of these signals (at low amplitudes of vibration) will be constant if the mechanical properties of the test body do not change.

The above method and device do not eliminate in a sufficiently wide range and with a required accuracy the influence of vibration on the accuracy of the test results, since the dependence of the residual field gradient on the distance to the surface of the test piece is non-linear.

Besides, the applicability of said method and device is limited to test pieces which are round in section.

DISCLOSURE OF INVENTION

The invention resides in the provision of a method and apparatus for magnetic testing of moving elongated ferromagnetic bodies, which, due to eliminating the influence of the test piece displacement caused by vibration and the changes in the velocity of said test piece on the test results, ensure a higher accuracy in determining mechanical properties of test pieces of any cross section.

The object of the invention is attained in a method of magnetic testing of moving elongated ferromagnetic body, which comprises magnetizing a portion of the test body by a pulsed magnetic field to thereby form within the remanent induction spot the regions magnetized to saturation in opposite directions, determining the quantity of the remanent magnetization which is used to judge the mechanical properties of the test piece and wherein according to the invention the quantity of the remanent induction is determined by converting the gradient of the remanent induction in a longitudinal direction of the magnetized portion to an electrical signal, selecting in this signal a pulse of one polarity indicative of the changes in the remanent magnetization between said regions, and integrating said selected pulse.

The object of the invention is also attained in an apparatus for magnetic testing of a moving elongated ferromagnetic test piece, which comprises a magnetizing pulse generator, magnetizing coils connected in antiparallel relationship to the output of the generator (connected such that the magnetic fields produced by them on the common axis thereof are directed towards each other), said coils embracing the test piece and located therealong, and a transducer embracing the test piece, adapted to convert the remanent magnetic field gradient to an electrical signal and connected to a measuring circuit connected with an indicator, and wherein according to the invention the measuring circuit comprises a key and an integrator connected in series therewith, and also a comparing circuit adapted to select a moment when the signal at the output of said transducer is passing through a zero, said comparison circuit having its input connected to the transducer and its output electrically connected to a control input of the key.

It is expedient that the comparison circuit be connected with the control input of the key preferably through a control unit, and the apparatus be constructed so that the output of the integrator is connected to the other input of the control unit through another comparison circuit for selecting a moment of time when the signal at the output of the integrator is zero, and the other output of the control unit is connected through a controlled current generator to the other input of the integrator. Such modification of the proposed device makes it possible to improve reproducibility of the test results at a greater embient temperature difference and provides a better noise immunity of the apparatus.

The proposed method and device eliminate the influence of the velocity of the test piece and desplacement thereof due to vibration on the accuracy of the test results, and allows the range of products for magnetic testing to be increased. The test results obtained with the aid of these method and apparatus are determined only by parameters of the spot of remanent induction, and therefore may represent with a high precision the mechanical properties of the test piece.

BRIEF DESCRIPTION OF DRAWINGS

The invention will now be explained in greater detail with reference to embodiments thereof which are represented in the accompanying drawings, in which.

BEST MODE FOR CARRYING OUT THE INVENTION

Figure 1:
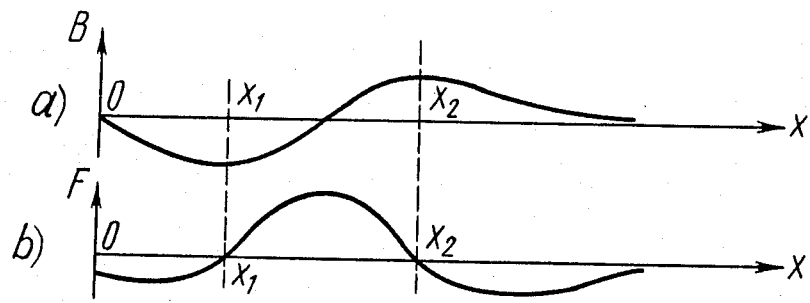
FIG. 1a represents a distribution curve of the remanent induction gradient along the test piece in the zone of magnetization according to the invention.
FIG. 1b illustrates the distribution of the remanent induction gradient at the zone of magnetization according to the invention.

The nature of the invention will be clear from the following description. A test piece is magnetized by a pulsed magnetic field to produce a spot of remanent induction. FIG. 1a illustrates a configuration of this spot having regions magnetized to saturation in opposite directions and located close to one another along the test piece. The function $B = B(\chi)$ describing said configuration of the induction spot is used hereinafter for the purpose of a fuller understanding of the nature of the invention. The gradient of the remanent induction, described by function $$F(x) = \frac{dB(x)}{dx}$$

(FIG. 1b) when the test piece is moving, is converted to an electric signal $\epsilon = \epsilon(t)$, where $\epsilon(t)$ is e.m.f. of the induction of the transducer for converting said gradient to an electric signal. Such transducer may be, for example, a measuring induction coil incorporated in the proposed apparatus which will be described below.

According to Faraday's law of induction the e.m.f. $\epsilon(t)$ of the coil induction is an exact differential of a given function $\phi(t)$ describing the variation in time of the quantity of the magnetic flux coupled with the coil $$\epsilon(t) = -\frac{d\phi(t)}{dt}$$

Therefore, the integral of the function $\epsilon(t)$ in a given time interval $(T_1, T_2)$ is determined only by the function $\phi(t)$ at instant of time $T_1$ and $T_2$. From Newton-Leibnitz's formula $$U = \int_{T_1}^{T_2} \epsilon(t)dt = -\int_{T_1}^{T_2} \frac{d\phi(t)}{dt} dt = \phi(T_1) - \phi(T_2)$$

According to the proposed method, irrespective of the velocity of the test piece, the instant of time $T_1$ corresponds to the passage of the test piece portion magnetized in one direction (section $X_2$ in FIG. 1a and b) through the transducer, and the instant of time $T_2$ corresponds to the passage through the transducer of the test piece portion magnetized to saturation in the opposite direction (section $X_1$), since at these instants the signal from the transducer, irrespective of the velocity of the test piece, equals zero (its polarity is reversed). Therefore, if a one-pole pulse is selected from the signal of the transducer and then integrated the following equation is obtained $$U = K[\phi(T_1) - \phi(T_2)] = K[\phi(X_2) - \phi(X_1)] = 2K \cdot \phi = 2 \cdot K[\int Bzds],$$

where $\phi(X_2)=\phi(T_1)=\phi$ is a magnetic flux passing through the transducer at the instant of time $T_1$ (start of integration), that is the remanent magnetic flux across the section $X_2$ of the test body; $\phi(X_1)=\phi(T_2)=-\phi$ is a magnetic flux passing through the transducer at the instant of time $T_2$ (termination of integration), that is the remanent magnetic flux across the section $X_1$ of the test piece; Br is a function of distribution of remanent induction over the section; K is a constant factor determined by the parameters of the transducer and the integrating device.

The thus obtained relationship does not include radial displacement of the test piece, caused by vibration, over the whole section area of the transducer, since at the instants of time $T_1$ and $T_2$ (for sections $X_2$ and $X_1$) practically the whole magnetic flux coupled with the coil is concentrated inside the test body. Said relationship does not depend on the velocity of the test piece moving through the transducer. The output signal is determined only by the quantity of remanent induction of the test piece and the shape of its section (i.e. by the quantity of remanent magnetic flux in the test body).

Figure 2:
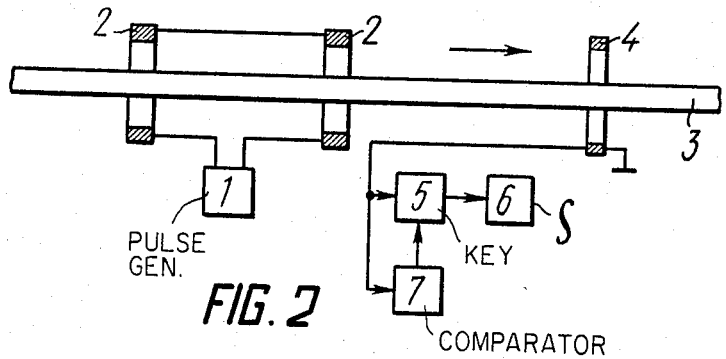
FIG. 2 is a block diagram of the proposed device.

The proposed method may be carried out with the aid of a device shown in FIG. 2. This device comprises a magnetizing pulse generator to the output of which are connected in anti-parallel relationship magnetizing coils 2'2' i.e., such that the fields produced by them on the common axis are directed towards each other. The coils 2'2' are located along the test piece 3 and embrace the latter. The distance between the magnetizing coils is selected depending on the real conditions under which the proposed method is carried out. The apparatus further includes a transducer for converting a gradient of remanent induction to an electrical signal. This transducer is preferably made in the form of a measuring coil 4. This coil embraces the test piece 3 and is connected to a measuring circuit which includes a key 5, an integrator 6, and a comparison circuit 7. The key 5 and the integrator 6 are connected in series to the coil 4. The comparison circuit 6 is adapted to select an instant of time when the signal from the coil 4 is passing through zero, and has its input connected to the latter. The output of the comparison circuit 7 is electrically connected with a control electrode of the key 5. The measuring circuit may be connected to any suitable recording device connected to the output of the integrator.

The apparatus operates as follows. The magnetizing pulse generator 1 generates pulses which are applied to the magnetizing coils 2, 2' which coils in response to said pulses form a remanent induction spot on the test piece (FIG. 1a). It is quite evident that such spots may be formed either periodically at required intervals or from time to time.

Figure 3:
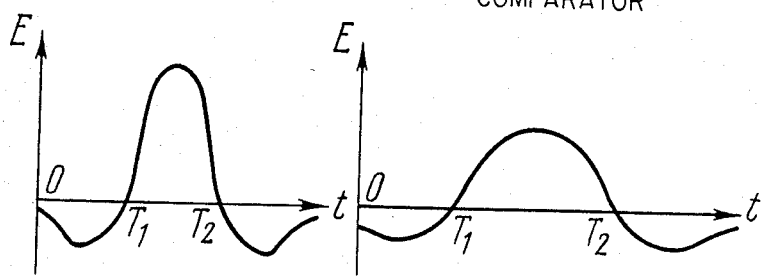
FIG. 3 represents signals at the output of the transducer at various velocities of the test piece according to the invention.
Figure 4:
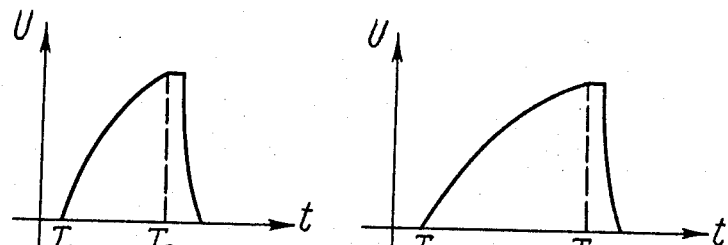
FIG. 4 is a time chart illustrating operation of the device shown in FIG. 2.

As the test piece 3 is passed through the measuring coil 4, the spot of remanent induction causes the latter to generate a signal $\epsilon(t)$ (FIG. 3). At the instant $T_1$ the portion magnetized to saturation in one direction passes through the measuring coil 4, the comparison circuit 7 operates to open the key 5. The integrator 6 starts integrating a signal applied from the measuring coil 4. At the instant $T_2$ the comparison circuit 7 operates again to close the key 5. Therefore, key 5 operates as a switch or gating means which passes the signal from transducer 4 to integrator 6 intermediate times $T_1$ and $T_2$. As a result, the output voltage of the integrator 6 will be proportional to the integral of the signal from the measuring coil 4 within a time interval $(T_1, T_2)$. This voltage is recorded and indexed by any suitable device (not shown in the drawings), whereafter the integrator is cleared and the measuring circuit is ready to start processing a next pulse. The time chart of the voltage at the output of the integrator 6 is shown in FIG. 4. The magnitude of the thus recorded signal is used to determine mechanical properties of the test piece.

Reproducibility of the test results at a greater ambient temperature difference and higher noise immunity of the apparatus may be advatageously ensured by employing a modification of the proposed device which is disclosed below.

Figure 5:
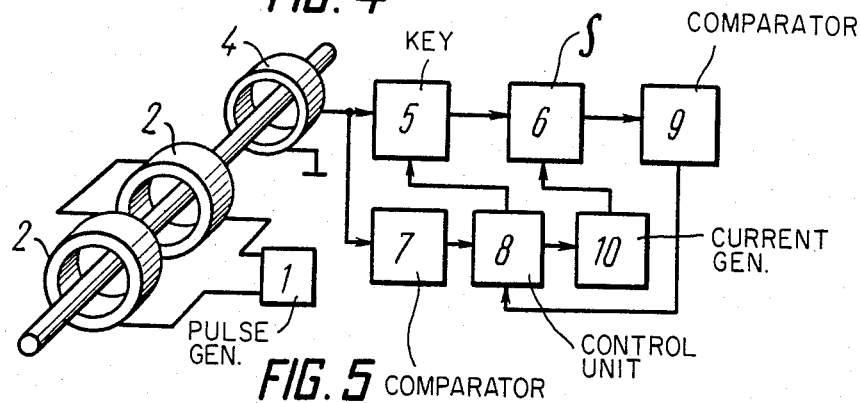
FIG. 5 shows another modification of the proposed device.

Referring now to FIG. 5, apart from the units shown in FIG. 5 the apparatus of this modification further includes a control unit 8 through which the comparison circuit 7 is electrically connected with the control input of the key 5. The output of the integrator 6 is connected to the other input of the control unit 8 through another comparison circuit 9 adapted to select an instant of time at which the output signal of the comparison circuit 6 is zero. The other output of the control unit 8 is connected through the controlled current generator 10 to the other input of the integrator, which output of the control unit may also be connected to any suitable device for recording the duration of the time interval for which the controlled current generator 10 is energized by the control unit 8.

$T_1$ and $T_2$ (FIG. 3) are instants of time at which the regions of the remanent induction spot in the test material magnetized to maximum in opposite directions pass through the measuring coils 4.

The apparatus of the above modification operates as follows. The moving test material is magnetized by the coils 2'2'. The shape of the remanent induction spot is shown in FIG. 1a. When through the measuring coil 4 is passed a non-magnetized portion of the test material 3, the signal at the output of the coil is zero. The key 5 is closed. The controlled current generator 10 is turned off. The output signal of the integrator 6 is zero. The remanent induction spot, when passing through the measuring coil 4, induces in said coil e.m.f. (FIG. 3). The comparison circuit 7 (FIG. 5) operates at the instant of time $T_1$. The control unit 8 opens the key 5 and the signal from the measuring coil 4 is applied to the integrator 6. The voltage at the output of said integrator increases proportionally $$\int_{T_1}^{t} \epsilon(t)dt.$$

As a result, the comparison circuit 9 operates (its threshold of operation determines the noise immunity of the device. At the instant of time $T_2$ (FIG. 3) the comparison circuit 7 operates again, in response to which control unit 8 causes the key 5 to close and the controlled current generator 10 to be turned on, whereby the capacitor (not shown) of the integrator 6 is caused to discharge by the current of said controlled current generator 10. When the voltage at the output of the integrator 6 is zero, the comparator 9 operates and the control unit 8 switches on the controlled current generator 10. The apparatus is ready to start processing a next pulse.

In this case the mechanical properties of the test material are determined by operating time of the controlled current generator 10. This time must be converted to a digital signal and applied to the indicator. If the controlled current generator 10 is a controlled d.c.

current generator, the time of operation thereof is proportional to the output voltage of the integrator 6 at the instant of time $T_2$ (FIG. 6), i.e.

$$\int_{T_1}^{T_2} \epsilon(t)dt$$

Figure 6:
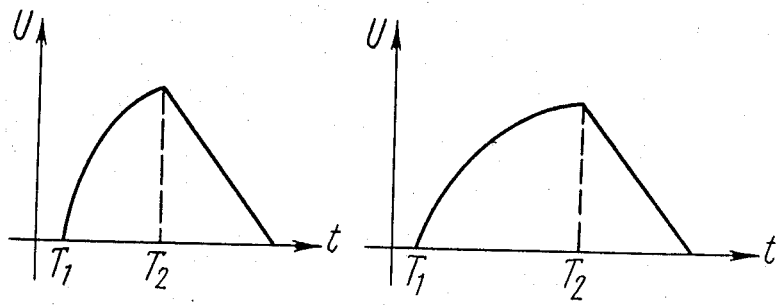
FIG. 6 is a time chart explaining operation of the device shown in FIG. 5.

(the time chart of the output voltage of the itegrator 6 is shown in FIG. 6). As is clear from the above description the value of this integral depends neither on the velocity of the test material nor. on the displacements thereof over the whole section area of the measuring coil 4, and is determined only by the parameters of the spot of remanent induction.

The described method and device enable elimination of an error which occurs in reading the data representative of the size of the spot of remanent induction, and which is caused by radial displacements of the test material and a non-linear dependence of the transducer signals on these displacements.

Furthermore, the proposed method and device rule out errors associated with the dependence of the signal being read on the velocity of the test material and twisting thereof.

INDUSTRIAL APPLICABILITY

The accuracy of measurement obtained by employing the proposed method and device allows, for example, testing of rolled product of any cross section, since the test material is not required to be necessarily symmetric in section. Therefore, the invention may be advantageously used for testing steel rolled product and pipes for mechanical properties during their manufacture.

What is claimed is:

1. A method for magnetic testing of a moving elongated ferromagnetic test piece for mechanical properties, which comprises:
   magnetizing a portion of the test piece by pulsed magnetic field to thereby form within the spot of remanent induction regions magnetized to saturation in opposite directions;
   concurrently moving the test piece;
   determining the magnitude of the remanent induction, which is used to judge the mechanical properties of the test piece, the magnitude of the remanent induction being determined by:
   converting the gradient of the remanent induction along the magnetized portion to an electrical signal;
   selecting in said electrical signal a one-polarity pulse indicative of the changes in the remanent induction between said regions; and,
   integrating said selected pulse.

2. A device for magnetic testing of a moving elongated ferromagnetic test piece, comprising:
   a magnetizing pulse generator;
   magnetizing coils embracing the test piece and being located therealong, said magnetizing coils are connecting to the magnetizing pulse generator such that the magnetic fields produced by them on the common axis thereof are directed towards each other;
   a transducer embracing the test piece adapted to convert a gradient of remanent induction to an electrical signal;
   a measuring circuit connected to the transducer;
   an indicator connected to the measuring circuit;
   the measuring circuit includes:
   a gating means and an integrator connected in series with said gating means, and a comparison circuit adapted to select an instant of time at which a signal at the output of the transducer assumes a zero value, said comparison circuit having its input connected to the transducer and its output electrically connected to a control input of the gating means.

3. A device as claimed in claim 2, wherein the electrical connection of the comparison circuit with the control input of the gating means is effected through a control unit, the output of the integrator is connected to the other input of the control unit through another comparison circuit adapted to select an instant of time at which a signal at the output of the integrator is zero, and the other output of the control unit is electrically connected through a controlled current generator to another input of the integrator.

* * * * *